US010296721B2

(12) United States Patent
Hanina et al.

(10) Patent No.: US 10,296,721 B2
(45) Date of Patent: May 21, 2019

(54) VERIFICATION OF MEDICATION ADMINISTRATION ADHERENCE

(71) Applicant: Ai Cure Technologies LLC, New York, NY (US)

(72) Inventors: Adam Hanina, New York, NY (US); Gordon Kessler, Mt. Kisco, NY (US)

(73) Assignee: Ai Cure Technology LLC, Mount Kisco, NY (US)

( * ) Notice: Subject to any disclaimer, the term of this patent is extended or adjusted under 35 U.S.C. 154(b) by 235 days.

(21) Appl. No.: 14/989,607

(22) Filed: Jan. 6, 2016

(65) Prior Publication Data

US 2016/0117482 A1 Apr. 28, 2016

Related U.S. Application Data

(63) Continuation of application No. 14/244,035, filed on Apr. 3, 2014, which is a continuation of application (Continued)

(51) Int. Cl.
| | |
|---|---|
| *G06F 19/00* | (2018.01) |
| *G06Q 10/10* | (2012.01) |
| *G06Q 50/22* | (2018.01) |
| *G06Q 50/24* | (2012.01) |
| *G06K 9/00* | (2006.01) |
| *G06T 7/00* | (2017.01) |

(52) U.S. Cl.
CPC ...... *G06F 19/3475* (2013.01); *G06F 19/3456* (2013.01); *G06K 9/00335* (2013.01); *G06K 9/00758* (2013.01); *G06Q 10/10* (2013.01); *G06Q 50/22* (2013.01); *G06Q 50/24* (2013.01); *G06T 7/0012* (2013.01)

(58) Field of Classification Search
CPC .... G06Q 50/22; G06Q 50/24; G06F 19/3418; G06F 19/3462; G06F 19/3456; G06F 19/00; G06F 19/3468; G06F 19/324; G06F 19/3475; G06F 19/325; G06F 19/32; G06F 19/34; G06F 11/3438; G16H 80/00; G16H 20/17; G16H 20/10
See application file for complete search history.

(56) References Cited

U.S. PATENT DOCUMENTS

| | | |
|---|---|---|
| 3,814,845 A | 6/1974 | Hurlbrink et al. |
| 5,065,447 A | 11/1991 | Barnsley et al. |
| (Continued) | | |

OTHER PUBLICATIONS

U.S. Appl. No. 14/244,035, filed Apr. 3, 2014, Hanina et al.
(Continued)

*Primary Examiner* — Joseph D Burgess
(74) *Attorney, Agent, or Firm* — Fish & Richardson P.C.

(57) ABSTRACT

A system and method of confirming administration of medication in a clinical trial is provided. The method comprises the steps of receiving information identifying a particular medication prescription regimen in accordance with the clinical trial, determining one or more procedures for administering such prescription regimen and identifying one or more activity sequences associated with such procedures. Activity sequences of actual administration of such prescription regimen are captured and then compared to the identified activity sequences to determine differences therebetween. A notice is provided if differences are determined.

19 Claims, 6 Drawing Sheets

Related U.S. Application Data

No. 13/558,380, filed on Jul. 26, 2012, now Pat. No. 8,731,961, which is a continuation of application No. 12/646,383, filed on Dec. 23, 2009, now abandoned.

(56) References Cited

U.S. PATENT DOCUMENTS

| | | | |
|---|---|---|---|
| 5,441,047 A | 8/1995 | David et al. |
| 5,544,649 A | 8/1996 | David et al. |
| 5,596,994 A | 1/1997 | Bro |
| 5,619,991 A | 4/1997 | Sloane |
| 5,646,912 A | 7/1997 | Cousin |
| 5,752,621 A | 5/1998 | Passamante |
| 5,764,296 A | 6/1998 | Shin |
| 5,810,747 A | 9/1998 | Brudny et al. |
| 5,911,132 A | 6/1999 | Sloane |
| 5,961,446 A | 10/1999 | Beller et al. |
| 5,963,136 A | 10/1999 | Obrien |
| 6,151,521 A | 11/2000 | Guo et al. |
| 6,233,428 B1 | 5/2001 | Fryer |
| 6,234,343 B1 | 5/2001 | Papp |
| 6,283,761 B1 | 9/2001 | Joao |
| 6,380,858 B1 | 4/2002 | Yarin et al. |
| 6,409,661 B1 | 6/2002 | Murphy |
| 6,421,650 B1 | 7/2002 | Goetz et al. |
| 6,483,993 B1 | 11/2002 | Misumi et al. |
| 6,484,144 B2 | 11/2002 | Martin et al. |
| 6,535,637 B1 | 3/2003 | Wootton et al. |
| 6,611,206 B2 | 8/2003 | Eshelman et al. |
| 6,628,835 B1 | 9/2003 | Brill et al. |
| 6,705,991 B2 | 3/2004 | Bardy |
| 6,879,970 B2 | 4/2005 | Shiffman et al. |
| 6,988,075 B1 | 1/2006 | Hacker |
| 7,184,047 B1 | 2/2007 | Crampton |
| 7,184,075 B2 | 2/2007 | Reiffel |
| 7,256,708 B2 | 8/2007 | Rosenfeld et al. |
| 7,277,752 B2 | 10/2007 | Matos |
| 7,304,228 B2 | 12/2007 | Bryden et al. |
| 7,307,543 B2 | 12/2007 | Rosenfeld et al. |
| 7,317,967 B2 | 1/2008 | DiGianfilippo et al. |
| 7,340,077 B2 | 3/2008 | Gokturk |
| 7,395,214 B2 | 7/2008 | Shillingburg |
| 7,415,447 B2 | 8/2008 | Shiffman et al. |
| 7,448,544 B1 | 11/2008 | Louie et al. |
| 7,562,121 B2 | 7/2009 | Berisford et al. |
| 7,627,142 B2 | 12/2009 | Kurzweil et al. |
| 7,657,443 B2 | 2/2010 | Crass et al. |
| 7,692,625 B2 | 4/2010 | Morrison et al. |
| 7,712,288 B2 | 5/2010 | Ramasubramanian et al. |
| 7,747,454 B2 | 6/2010 | Bartfeld et al. |
| 7,761,311 B2 | 7/2010 | Clements et al. |
| 7,769,465 B2 | 8/2010 | Matos |
| 7,774,075 B2 | 8/2010 | Lin et al. |
| 7,874,984 B2 | 1/2011 | Elsayed et al. |
| 7,881,537 B2 * | 2/2011 | Ma .................. G06K 9/00348 |
| | | | 382/103 |
| 7,908,155 B2 | 3/2011 | Fuerst et al. |
| 7,912,733 B2 | 3/2011 | Clements et al. |
| 7,945,450 B2 | 5/2011 | Strawder |
| 7,956,727 B2 | 6/2011 | Loncar |
| 7,983,933 B2 | 7/2011 | Karkanias et al. |
| 8,065,180 B2 | 11/2011 | Hufford et al. |
| 8,321,284 B2 | 11/2012 | Clements et al. |
| 8,370,262 B2 | 2/2013 | Blessing |
| 8,606,595 B2 | 12/2013 | Udani |
| 2001/0049673 A1 | 12/2001 | Dulong et al. |
| 2001/0056358 A1 | 12/2001 | Dulong et al. |
| 2002/0026330 A1 | 2/2002 | Klein |
| 2002/0093429 A1 | 7/2002 | Matsushita et al. |
| 2002/0143563 A1 | 10/2002 | Hufford et al. |
| 2003/0036683 A1 | 2/2003 | Kehr et al. |
| 2003/0058341 A1 | 3/2003 | Brodsky et al. |
| 2003/0164172 A1 | 9/2003 | Chumas et al. |
| 2003/0190076 A1 | 10/2003 | Delean |
| 2003/0225325 A1 | 12/2003 | Kagermeier et al. |
| 2004/0100572 A1 | 5/2004 | Kim |
| 2004/0107116 A1 | 6/2004 | Brown |
| 2004/0155780 A1 | 8/2004 | Rapchak |
| 2005/0144150 A1 | 6/2005 | Ramamurthy et al. |
| 2005/0149361 A1 | 7/2005 | Saus et al. |
| 2005/0180610 A1 | 8/2005 | Kato et al. |
| 2005/0182664 A1 | 8/2005 | Abraham-Fuchs et al. |
| 2005/0234381 A1 | 10/2005 | Niemetz et al. |
| 2005/0267356 A1 | 12/2005 | Ramasubramanian et al. |
| 2006/0066584 A1 | 3/2006 | Barkan |
| 2006/0218011 A1 | 9/2006 | Walker et al. |
| 2006/0238549 A1 | 10/2006 | Marks |
| 2006/0294108 A1 | 12/2006 | Adelson et al. |
| 2007/0008112 A1 | 1/2007 | Covannon et al. |
| 2007/0008113 A1 | 1/2007 | Spoonhower et al. |
| 2007/0030363 A1 | 2/2007 | Cheatle et al. |
| 2007/0118389 A1 | 5/2007 | Shipon |
| 2007/0194034 A1 | 8/2007 | Vasiadis |
| 2007/0233035 A1 | 10/2007 | Wehba et al. |
| 2007/0233049 A1 | 10/2007 | Wehba et al. |
| 2007/0233050 A1 | 10/2007 | Wehba et al. |
| 2007/0233281 A1 | 10/2007 | Wehba et al. |
| 2007/0233520 A1 | 10/2007 | Wehba et al. |
| 2007/0233521 A1 | 10/2007 | Wehba et al. |
| 2007/0273504 A1 | 11/2007 | Tran |
| 2007/0288266 A1 | 12/2007 | Sysko et al. |
| 2008/0000979 A1 | 1/2008 | Poisner |
| 2008/0076973 A1 * | 3/2008 | Muradia .................. G16H 10/60 |
| | | | 600/300 |
| 2008/0093447 A1 | 4/2008 | Johnson et al. |
| 2008/0114226 A1 | 5/2008 | Music et al. |
| 2008/0114490 A1 | 5/2008 | Jean-Pierre |
| 2008/0119958 A1 | 5/2008 | Bear et al. |
| 2008/0138604 A1 | 6/2008 | Kenney et al. |
| 2008/0140444 A1 | 6/2008 | Karkanias et al. |
| 2008/0162192 A1 | 7/2008 | Vonk et al. |
| 2008/0172253 A1 | 7/2008 | Chung et al. |
| 2008/0178126 A1 | 7/2008 | Beeck et al. |
| 2008/0201174 A1 | 8/2008 | Ramasubramanian et al. |
| 2008/0219493 A1 | 9/2008 | Tadmor |
| 2008/0275738 A1 | 11/2008 | Shillingburg |
| 2008/0290168 A1 | 11/2008 | Sullivan et al. |
| 2008/0297589 A1 | 12/2008 | Kurtz et al. |
| 2008/0303638 A1 | 12/2008 | Nguyen et al. |
| 2009/0012818 A1 | 1/2009 | Rodgers |
| 2009/0018867 A1 | 1/2009 | Reiner |
| 2009/0043610 A1 | 2/2009 | Nadas et al. |
| 2009/0048871 A1 | 2/2009 | Skomra |
| 2009/0095837 A1 | 4/2009 | Lindgren |
| 2009/0128330 A1 | 5/2009 | Monroe |
| 2009/0159714 A1 | 6/2009 | Coyne, III et al. |
| 2009/0217194 A1 | 8/2009 | Martin et al. |
| 2009/0245655 A1 | 10/2009 | Matsuzaka |
| 2010/0042430 A1 | 2/2010 | Bartfeld |
| 2010/0050134 A1 | 2/2010 | Clarkson |
| 2010/0057646 A1 | 3/2010 | Martin et al. |
| 2010/0092093 A1 | 4/2010 | Akatsuka et al. |
| 2010/0136509 A1 | 6/2010 | Mejer et al. |
| 2010/0138154 A1 | 6/2010 | Kon |
| 2010/0255598 A1 | 10/2010 | Melker |
| 2010/0262436 A1 | 10/2010 | Chen et al. |
| 2010/0316979 A1 | 12/2010 | Von Bismarck |
| 2011/0021952 A1 | 1/2011 | Vallone |
| 2011/0119073 A1 | 5/2011 | Hanina et al. |
| 2011/0153360 A1 | 6/2011 | Hanina et al. |
| 2011/0161109 A1 | 6/2011 | Pinsonneault et al. |
| 2011/0195520 A1 | 8/2011 | Leider et al. |
| 2011/0275051 A1 | 11/2011 | Hanina et al. |
| 2012/0011575 A1 | 1/2012 | Cheswick et al. |
| 2012/0075464 A1 | 3/2012 | Derenne et al. |
| 2012/0081551 A1 | 4/2012 | Mizuno et al. |
| 2012/0140068 A1 | 6/2012 | Monroe et al. |
| 2012/0182380 A1 | 7/2012 | Ohmae et al. |

OTHER PUBLICATIONS

U.S. Appl. No. 13/558,380, filed Jul. 26, 2012, Hanina et al.
U.S. Appl. No. 12/646,383, filed Dec. 23, 2009, Hanina et al.

(56) References Cited

OTHER PUBLICATIONS

Ammouri, S.; Biloduau, G. -A, "Face and Hands Detectionand Tracking Applied to the Monitoring of Medication Intake," Computer and Robot Vision, 2008. CRV '08. Canadian Conference on, vol. No., pp. 147, 154, May 28-30, 2008.
Batz, et al. "A computer Vision System for Monitoring Medicaiton Intake," in Proc. IEEE 2nd Canadian Conf. on Computer and Robot Vision, Victoria, BC, Canada, 2005, pp. 362-369.
Bilodeau et al. Monitoring of Medication Intake Using a Camera System. Journal of Medical Systems 2011. [retrieved on Feb. 18, 2013] Retrieved from ProQuest Technology Collection.
Chen, Pauline W., "Texting as a Health Tool for Teenagers", The New York Times, Nov. 5, 2009, http://www.nytimes.com/2009/11/05/health/05chen.html?_r=1&emc=.
Danya International, Inc., "Pilot Study Using Cell Phones for Mobile Direct Observation Treatment to Monitor Medication Compliance of TB Patients", Mar. 20, 2009, www.danya.com/MDOT.asp.
Final Office Action from PTO, Cited in AI-0001-U1 (U.S. Appl. No. 12/620,686), (dated May 8, 2012), 1-24.
Final Office Action from PTO, Cited in AI-0001-U2 (U.S. Appl. 13/558,377), dated May 7, 2013, 1-29.
Final Office Action from PTO, Cited in AI-0002-U1 (U.S. Appl. No. 12/646,383), (dated May 8, 2012), 1-31.
Final Office Action from PTO, Cited in AI-0002-U2 (U.S. Appl. No. 13/588,380), (dated Mar. 1, 2013), 1-27.
Final Office Action from PTO, Cited in AI-0003-U1 (U.S. Appl. No. 12/646,603), (dated Feb. 1, 2012), 1-17.
Final Office Action from PTO, Cited in AI-0004-U1 (U.S. Appl. No. 12/728,721), (dated Apr. 12, 2012), 1-31.
Final Office Action from PTO, Cited in AI-0005-U1 (U.S. Appl. No. 12/815,037), (dated Sep. 13, 2012), 1-15.
Final Office Action from PTO, Cited in AI-0006-U1 (U.S. Appl. No. 12/899,510), (dated Aug. 28, 2013).
Final Office Action from PTO, Cited in AI-0008-U1 (U.S. Appl. No. 12/898,338), dated Nov. 9, 2012), 1-12.
Final Office Action from PTO, Cited in AI-0012-U1 (U.S. Appl. No. 13/189,518), (dated Jul. 23, 2013), 1-16.
Global Tuberculosis Control: A short update to the 2009 report, World Health Organization, (2009).
Huynh et al., "Real time face detection, tracking and recognition of medication intake." World Academy of Science, Engineering and Technology 60 (2009), 280-287.
International Preliminary Report on Patentability, cited in AI-0001-PCT1 (PCT/US2010/056935) (dated May 31, 2012), 1-8.
Mintchell, "Exploring the Limits of Machine Vision", Automating World, Oct. 1, 2011.
Non-Final Office Action from PTO, Cited in AI-0001-U1 (U.S. Appl. No. 12/620,686), (dated Dec. 21, 2011),1-78.
Non-Final Office Action from PTO, Cited in AI-0001-U2 (U.S. Appl. No. 13/558,377), (dated Oct. 22, 2012), 1-21.
Non-Final Office Action from PTO, Cited in AI-0002-U1 (U.S. Appl. No. 12/646,383), (dated Dec. 22, 2011),1-78.
Non-Final Office Action from PTO, Cited in AI-0002-U2 (U.S. Appl. No. 13/558,380), (dated Oct. 4, 2012), 1-20.
Non-Final Office Action from PTO, Cited in AI-0003-U1 (U.S. Appl. No. 12/646,603), (dated Oct. 13, 11),1-74.
Non-Final Office Action from PTO, Cited in AI-0003-U1 (U.S. Appl. No. 12/646,603), (dated Jun. 13, 2013), 1-16.
Non-Final Office Action from PTO, Cited in AI-0004-U1 (U.S. Appl. No. 12/728,721), (dated Jan. 6, 2012), 1-31.
Non-Final Office Action from PTO, Cited in AI-0004-U1 (U.S. Appl. No. 12/728,721), (dated May 9, 2013), 1-25.
Non-Final Office Action from PTO, Cited in AI-0005-U1 (U.S. Appl. No. 12/815,037), (dated Mar. 28, 2012),1-17.
Non-Final Office Action from PTO, Cited in AI-0005-U1 (U.S. Appl. No. 12/815,037), (dated Jul. 18, 2013), 1-19.
Non-Final Office Action from PTO, Cited in AI-0006-U1 (U.S. Appl. No. 12/899,510), (dated Jan. 23, 2013), 1-20.
Non-Final Office Action from PTO, Cited in AI-0008-U1 (U.S. Appl. No. 12/898,338), (dated Jun. 19, 2012), 1-16.
Non-Final Office Action from PTO, Cited in AI-0012-U1 (U.S. Appl. No. 13/189,518), (dated Dec. 21, 2012), 1-10.
Non-Final Office Action from PTO, Cited in AI-0013-U1 (U.S. Appl. No. 13/235,387), dated Sep. 12, 2013), 1-16.
Osterberg, Lars and Blaschke, Terrence, "Adherence to Medication", New England Journal of Medicine 2005; 353:487-97, Aug. 4, 2005.
PCT Search report and written opinion, Cited in AI-0001-PCT1 (PCT/US2010/56935, (dated Dec. 1, 2011),1-9.
PCT Search report and written opinion, Cited in AI-0005-PCT1 (PCT/US2011/35093, (dated Dec. 9, 2011),1-8.
PCT Search report and written opinion, Cited in AI-0006-PCT1 (PCT/US11/54666), (dated Feb. 28, 2012), 1-13.
PCT Search report and written opinion, Cited in AI-0008-PCT1 (PCT/US11/54668), dated Feb. 28, 2012, 1-12.
PCT Search report and written opinion, Cited in AI-0012-PCT1 (PCT/US12/41785), (dated Aug. 17, 2012),1-10.
PCT Search report and written opinion, Cited in AI-0013-PCT1 (PCT/US12/42843), (dated Aug. 31, 2012), 1-8.
PCT Search report and written opinion, Cited in AI-0018-PCT1 (PCT/US2012/051554), (dated Oct. 19, 2012), 1-12.
PCT Search report and written opinion, Cited in AI-0019-PCT (PCT/US12/59139), (dated Dec. 18, 2012), 1-15.
PCT Search report and written Opinion, Cited in AI-0020-PCT1 (PCT/US13/20026), (dated May 8, 2013), 1-14.
Super-Resolution, Wikipedia, (Oct. 5, 2010).
University of Texas, GuideView, Mar. 15, 2007, http://www.sahs.uth.tmc.edu/MSriram/GuideView/.
Valin, et al. "Video Surveillance of Medication intake", Int. Conf. of the IEEE Engineering in Medicine and Biology Society, New York City, USA, Aug. 2006.
Wang et al. "Recent Developments in human motion analysis." Pattern Recognition 36 (220) 585-601 (Nov. 2001).
Whitecup, Morris S., "2008 Patient Adherence Update: New Approaches for Success", www.guideline.com, The Trend Report Series, (Oct. 1, 2008).
V.F.S. Fook et al. "Smart Mote-Based Medical System for Monitoring and Handling Medication Among Persons with Dementia. "ICOST 2007, LNCS 4541, pp. 54-62, 2007.
PR Newswire. "Pilot Study Using Video Cell Phones for Mobile Direct Observation (MOOT) to Monitor Medication Compliance of TB Patients." New York: Mar. 23, 2009.

\* cited by examiner

VERIFICATION OF MEDICATION ADMINISTRATION ADHERENCE

This application is a continuation application of U.S. patent application Ser. No. 14/244,035, filed Apr. 3, 2014 to Hanina et al., entitled "Method and Apparatus for Verification of Medication Adherence," currently pending, which, in turn, is a continuation application of U.S. patent application Ser. No. 13/558,380, filed Jul. 26, 2012 to Hanina et al. entitled "Method and Apparatus for Verification of Clinical Trial Adherence", now U.S. Pat. No. 8,731,961, issued May 20, 2014, which, in turn, is a continuation application of U.S. patent application Ser. No. 12/646,383, filed Dec. 23, 2009, to Hanina et al., entitled "Method and Apparatus for Verification of Clinical Trial Adherence", currently abandoned. The contents of all of the prior applications are incorporated herein by reference in their entirety.

FIELD OF THE INVENTION

This invention relates generally to patient compliance in clinical drug trials and more particularly to the monitoring, instruction and intervention of patients in clinical trials in order to improve compliance with required drug protocols in accordance with those trials.

BACKGROUND OF THE INVENTION

Dr Lars Osterberg, M.D. and Dr, Terence Blaschke have reported in the New England Journal of Medicine, *Adherence to Medication*, (N Engl J Med 2005; 353:487-97) 2005 an alarming lack of adherence to required medication protocol, further noting that while the average rates of adherence in clinical trials is categorized as "high", this number still comprises only rates of 43 to 78 percent. Most importantly, the authors note "The ability of physicians to recognize nonadherence is poor, and interventions to improve adherence have had mixed results." *Adherence*, p. 487. The authors conclude "Poor adherence to medication regimens is common, contributing to substantial worsening of disease, death and increased healthcare costs." *Adherence*, p. 494. *The Trend Repot Series,* 2008 *Patient Adherence Update: New Approaches for Success,* October 2008, report similar discouraging statistics. This broad range may possibly contribute to the public confidence in the FDA approval process and the importance of continued surveillance of a drug throughout the process. Furthermore, it may help to explain why, according to the Journal of the American Medical Association (JAMA May 1, 2002), one out of every five new drugs that comes to market in the US is found to have serious or life-threatening adverse effects—unknown or undisclosed at the time of approval. It is against this backdrop of poor adherence, and potential danger to patients, that the present invention operates.

It has been widely recognized that methods and systems for insuring proper medication ingestion or administration by individuals are very important in defending against unnecessary sickness, deaths and other problems. Giving instructions and then letting patients fend for themselves has been shown not to work particularly well. This is because it is not only the improper ingestion of medicines that is the primary cause of medical danger. Rather, an overall lack of sufficient patient guidance is also part of the problem. Further, the inability to confirm a proper prescription regimen being provided to a user in the first place may cause a number of other problems with the use of such medication.

These issues are even more problematic in a clinical trial setting where a lack of adherence to a particular assigned protocol may influence eventual approval of a particular drug therapy, potentially denying a valuable drug to the public and resulting in possible rejection of drugs that should be on the market that have been backed by pharmaceutical companies for hundreds of millions of dollars. Additionally, failure to adhere to prescribed protocols in clinical drug trials may result in poor data collection and evaluation, thus resulting in the above mentioned deaths from failure for trials to identify potentially life-threatening side effects. Poor adherence to prescribed protocols in clinical drug trials may refer to any deviation in a patient's behavior from that recommended by the trial designers, including, in addition to improper medication administration, improper timing of administration, such areas as dietary advice, advice on smoking, or even advice about attendance for further investigation or follow-up. Specifically in clinical trials, any such poor pharmaceutical compliance by the patient may result in inadequate results or outcomes.

Corrupt or incomplete clinical trial data, inefficiency in following drug regimens and the inherent liability involved with clinical trials further complicate an already time consuming, complex, and expensive approval process which may take between 8 to 12 years and cost over $900 million. Even after the initial clinical trial testing has been completed, there is generally no system for monitoring further use in Phase IV testing, or monitoring patients after launch. Given the possibility of failure of the clinical trial testing to ensure drug safety, such additional testing may be quite important. Inherent to the clinical trial process are a number of common mistakes that have not yet been addressed with existing clinical trial protocols.

Traditionally, participants attend introductions and follow ups for clinical trials in-person. Data collection is similarly limited to patient visits, rather than on a daily basis. Old methods such as patient questioning and pill counting have been proven to be inadequate measures of adherence and offer no information on dose timing and drug holidays (omission of medication for three or more sequential days).

Compliance technologies can increase the statistical power of clinical trials. Through the use of such technology, clinical events can be precisely linked to medication use history. Captured data can be linked to other sources such as EDC, patient diaries and data collected by the physician. Technologies can create many possibilities for remote visits and data capture. While smart packaging technologies exist such as RFID-enabled computer chip technology, smart blister packs and MEMS caps (microprocessor in a bottle cap), they are: a) invasive and need to be physically attached to the medications; b) are non-conclusive regarding compliance—a patient may activate the technology without ingestion of the medication; c) remain largely unadopted in clinical trials by the pharmaceutical and biotech companies due to their high cost; and d) take a longer time to implement.

Jo Carol et al. stated that "The most reliable method for research purposes, although not practical in a clinical setting, may be a combination approach that includes pill counts, patient self-report, and electronic monitoring." (Carol J. et al, Patterns to Antiretroviral Medication, The Value of Electronic Monitoring, AIDS, 17 (12), pp 1, 763-767, October 2003. To date, technologies alone have only been used to monitor compliance rather than to encourage it. Furthermore, there has been no comprehensive system provided that allows for the management of multiple patients and multiple patient populations. While current technology may allow poor compliers to be recognized, as will be described below, the proposed system of the present invention will help to encourage pharmaceutical compliance and tackle some of the problems that are encountered in the clinical trial process.

Another problem is the issue of informed consent and the protection many clinical trials attempt to implement, often unsuccessfully, to protect themselves from potential lawsuits. A survey was conducted by CenterWatch (Getz, K. A. (2002). *Informed consent process: A survey of subjects assesses strengths and weaknesses Applied Clinical Trials*, 11(11), 30-36) to assess subjects' understanding of the consent documents further supports the concept that patients may not understand the forms they are signing. The survey reported that 14% of patients signed a consent document without reading the form. In the same survey, 30% of patients reported that they did not understand that their trial could carry more risk and discomfort than standard treatment. Nearly 40% of patients did not know that they could call an ethics board or IRB representative with questions about problems or concerns. The survey reported that 41% of patients did have study nurses review the consent form with them. The survey finally concluded that 70% of the participants may not have known what questions to ask at the outset of the informed consent process. And, this is with the current information provided and consent received from these participants. With approximately 77,967 trials in as many as 172 countries registered with ClinicalTrials.gov as of the date of this application, the logistical challenge of ensuring consistency is overwhelming.

In patients with psychiatric illness, adherence may be even more difficult and technology solutions such as the one proposed in accordance with the present invention may offer accurate ways to authenticate adherence. According to Cramer and Rosenhek (Compliance with Medication regimens for mental and physical disorders, Psychiatr Serv 1998), among patients with physical disorders, the mean rate of medication adherence was 76%, whereas among those with psychoses the mean rate was 58% and among those with depression the mean rate was 65%. Similar compliance issues might be expected to be present when dealing with child patients, or others who may have difficulty following potentially confusing instructions.

The logistical challenge of medication adherence and auditing in clinical trials is certainly increasing, with more than 70,000 clinical trials under way throughout the world, growing at a rate of 8 to 10 percent a year, according to CenterWatch in Boston, which lists clinical trials. In 2003, there were 3.6 million individuals enrolled in clinical trials in the United States, according to the center. Self-regulation in the industry is necessary as the FDA inspected only 1% of clinical trial sites during the 2000 to 2005 period (Department of Health and Human Services, Food and Drug Administration's Oversight of Clinical Trials, September 2007). As the requirements for drugs increase, one can expect that the ability for the FDA to inspect such clinical trial sites to decrease even further. Furthermore, the average cost of $6533 to recruit a patient for a trial, and three times that amount to recruit a new patient if one is lost due to noncompliance is high so pre-screening subjects and monitoring them on an ongoing basis is critical. These numbers are significant given the fact that it has been calculated that if 30% of patients in a clinical trial had inadequate compliance, double the number of patients would need to be studied to create the same alpha and beta levels (Pledger G W. Compliance in clinical trials: impact on design, analysis and interpretation. Epilepsy Research 1988; 2 (suppl): 125-33).

*Tufts CSDD Impact Report* stated that within three years, major sponsors project that up to 65% of FDA-regulated clinical trials will be conducted outside the U.S.—primarily in Central and Eastern Europe, Latin America, India, and Asia—due to economic advantages and ready access to well-trained physicians and large numbers of treatment-naïve patients. In addition, contract clinical services account for more than 17% of total drug development spending. The growth of sponsor spending on CRO (Clinical Research Organization) services will outpace overall growth in spending on global drug development for the foreseeable future, reflecting increasing reliance on contract providers to provide added capacity, more flexibility, and greater efficiency.

With greater amounts of clinical trials being conducted abroad, technology can aid standardization and provide greater communication where deficiencies in existing infrastructure such as physician and nurse training, may exist.

A number of systems exist that provide instructions to a user regarding when to take a medication and records when the user indicates that a medication has been taken. U.S. Pat. No. 7,359,214 describes such a system. A device is provided that provides instruction to a patient regarding medications to take. Furthermore, the system may provide a method for determining that the prescription is appropriate given the patient's conditions, and other medications he or she may already be taking. The system may monitor the dispensing of medicine in accordance with a predetermined treatment protocol. While such a system provides many improvements for easing a burden on the patient, this system suffers in many ways and in particular in ways relevant to the administration of clinical trials.

Most importantly, this system provides no mechanism for actually confirming that a patient is in fact ingesting or otherwise properly administering required medication as required in a clinical drug trial. While the system may be sufficient for one who is in full possession of their mental faculties, any individual who may have difficulty following directions, or one who is actively avoiding medication may still not be taking required medication after it is dispensed. Thus, participants may be forgetful, visually impaired, or otherwise do not believe in the benefit of taking such medication, and may thus not properly log medication administration. Furthermore, the system requires preloading of various medications into a dispenser, and thus likely requires regular visits by an administering manager to be sure appropriate medications are in fact properly loaded therein. It is surely possible that an inexperienced user may place incorrect medications into the device, or may somehow provide incorrect dosages into the device. Additionally, for potentially more complex regimens, there is no method provided for insuring that a user is able to follow such a protocol, and to thereafter confirm that the user has in fact taken all required medications in accordance with any provided instructions or the like, or has taken the medications according to one or more specifications or followed suggested procedures. Furthermore, this system is expensive and requires constant maintenance to confirm that the various mechanical parts are in working order.

U.S. patent application Ser. No. 11/839,723, filed Aug. 16, 2007, titled Mobile Wireless Medication Management System provides a medication management system employing mobile devices and an imaging technology so that a user is able to show a pill to be taken to the system, and the system can then identify the medication. Patient histories are available to an administrator, including various vital signs as measured by the system. Images may also be taken of the patient, provider, medication container or the like. While the system professes to ensure adherence to a protocol, the system only provides such help if requested by a user. There is in fact no particular manner in which to ensure actual adherence or the relationship of adherence to the efficacy of the drug over time. When requiring adherence to a predetermined protocol for a clinical trial, this is particularly relevant.

Additionally, existing systems fail to maintain an audit trail for post administration review by a medical official or other clinical trial administrator, and further cannot therefore confirm confirmation of proper medication administration.

Therefore, it would be desirable to provide a method and apparatus that overcomes the drawbacks of the prior art.

SUMMARY OF THE INVENTION

In accordance with the present invention, a system and method are provided that allow for complete control and verification of adherence to a prescribed medication protocol or machine or apparatus use in a clinical trial setting, whether in a health care provider's care, or when self administered in a homecare situation by a patient.

The present invention is intended for the clinical trial market as a full audit and tracking tool for pharmaceutical compliance in subjects. The invention provides the only medication management system that may determine whether a user is actually following a protocol, provide additional assistance to a user, starting with instructions, video instructions, and the like, and moving up to contact from a medication administrator if it is determined that the user would need such assistance. Upon prescription of a medication to a user in a clinical trial, the trial designers may then select a desired protocol for the user to follow, and therefore, not only may a particular drug be tested, but also test the ease of adherence given a particular set of instructions.

In recent years, the United States Department of Health and Human Services, Office of the Inspector General ("OIG") has issued publications to make it clear to members of the boards of directors of health care companies conducting business with federal health care programs (directly or indirectly) that these fiduciary duties include an obligation at the board level to assure that the health care company maintains an effective corporate compliance program. Due to increased compliance obligations by the office of the inspector general (OIG), chief compliance officers of pharmaceutical companies must, to best of their knowledge, ensure that their company is compliant with any required regulations. Failure may result in personal liability. Thus, the ability to maintain an audit trail in a clinical trial setting may aid in meeting these requirements.

The novel combination of text, graphical, pictorial, and video allows the compliance problem within clinical trials to be tackled in a holistic manner. The system in accordance with the present invention offers a number of solutions. First, the system helps to ensure that the patient is giving informed consent. The system and method may provide step-by-step image and video instructions to the user or care provider on how to administer the medication, what the side effects of the medication are and the benefits that have been found. This avoids misunderstandings resulting from prescribing instructions and may allow an approach that may be utilized internationally, thus overcoming possible language barrier issues and the like.

A specific medication regimen may be programmed into a medication calendar to alert the user when medication should be taken and provide clear video instruction for taking the medication. These reminders minimize forgetfulness by the subject in clinical trials and help the logistical challenges involved in complex medication regimen such as double blind studies, for example. Furthermore, the medication calendar and the compliance results are accessible to the clinical trial organizers.

Once an alert is made and the patient has confirmed that they are ready to take the medication, the system and method of the invention record the type of medication and quantity through image recognition. The subject shows the medication to an imaging device which then authenticates the medication if in the correct dosage and offer administration instructions. Other types of recognition of the bottles may also be used, including RFID tags, bar code reading, text recognition, or other confirmation through a provided graphical user interface, preferably in conjunction with the image recognition. Once the medication type and quantity has been authenticated, the system and method of the invention records or otherwise visually analyzes the patient actually administering the medication to him or herself, using any of the above recognition methods, and further including facial recognition, badge identification, or any other method for confirming the identity of the individual. A real-time log for audit trails and further analysis is thereby created. Additional information may be captured using a brief questionnaire on the device which may help to highlight problems when administering the medication—such as difficulty in swallowing tablets or opening packages—or adverse reactions from which the patient is suffering. Whatever the reason a patient misses a reminder or medication prompt, the system and method of the invention alerts the clinical trial organizers. Data from all the population can be captured and presented in an aggregated manner online in real-time, giving real-time data results and flag problems or results early.

As clinical trials begin, it will quickly become evident if a clinical trial is designed well and difficulties or non-compliance will be highlighted by the system and method of the invention. Often inconvenient or restrictive precautions prevent the medication regimen from being followed accurately and this type of feedback can be very useful. The system of the invention minimizes delinquent or inaccurate data submission by linking clinical events to medication use. The system also tracks the actions taken when a problem has been highlighted. This audit trail is then stored. Finally, if a patient is determined to be unable to follow a prescribed regimen, that patient may be identified and removed from the clinical trial population, or at least flagged, thus removing a confounding factor from the determination of whether a drug is safe and effective.

The system and method preferably includes a means for receiving user medication information, including a medication profile and history, providing indications to a user regarding when to take a medication in accordance with a prescribed regimen in accordance with a clinical trial, and which medication to take, imaging medication either in pill or container form to confirm that a correct medication is being taken, confirming, in accordance with the user medication, that a new medication prescribed in accordance with a clinical trial will not conflict with another medication the user is already taking (including non-prescription medication that may be used by a patient), scan a group of medication containers or pills to inform a user which is the correct medication through the use of visual, verbal or other prompts, providing assistance information to aid a user in properly taking the medication, imaging, employing still photos, video sequences or other activity or gesture recognition techniques, the user to confirm that the medication is being actually and properly taken, providing any appropriate additional or special instructions so that the user is able to comply with the instructions of the clinical trial, using the imaging to note any possible adverse effects associated with taking of the medication, accumulating statistics about adherence to a prescribed protocol, assisting in reordering medication on an as-needed basis and notifying a clinical trial manager if the user is not properly following a prescribed protocol. If desired, a patient's face or other identifying features may be hidden so that the recorded sequences may be stored, displayed and otherwise used without allowing the identity of any particular patient to be released.

From beginning to end, a user is provided with a system and method that aids the user in properly following a protocol as defined in a clinical trial setting, while informing an administrator of any deviations from the protocol, either innocent or purposeful, by a user so that an early intervention may be provided. The present invention is the only clinical trial medication adherence verification system that may determine whether a user is actually following a protocol, and provide additional assistance to a user, starting with instructions, video instructions, and the like, and moving up to intervention from a medication administrator through phone, email video conferencing or the like, if it is determined that the user may benefit from such assistance. Through such improved provision of care, potential clinical trial participants may be more likely to participate in such a clinical trial. The system may also identify individuals to be removed from a clinical trial population, and also possibly identify sets of instructions that may not be working to get people to follow the prescribed regimen.

Still other objects and advantages of the invention will in part be obvious and will in part be apparent from the specification and drawings.

The invention accordingly comprises the several steps and the relation of one or more of such steps with respect to each of the others, and the apparatus embodying features of construction, combinations of elements and arrangement of parts that are adapted to affect such steps, all as exemplified in the following detailed disclosure, and the scope of the invention will be indicated in the claims.

BRIEF DESCRIPTION OF THE DRAWINGS

For a more complete understanding of the invention, reference is made to the following description and accompanying drawings, in which.

DETAILED DESCRIPTION OF THE PREFERRED EMBODIMENTS

In accordance with the invention, a system and process are provided that improve adherence to medical protocol in a clinical trial setting, and give administrators a tangible and concrete manner in which to confirm compliance or lack thereof, and the ability to intervene early in the process to ensure that patients enrolled in such a clinical trial study are properly taking their medication. The system and method of the invention provide for instructions to patients on the use of the prescription medication under trial, verification to a doctor or other service provider of patient adherence to the prescribed protocol, and statistical and individual analysis of adherence rates to ensure proper clinical trial administration. The system and method further improve a level of care received by a patient in a clinical trial, and other setting, as well as improve the perception of that level of care by the patient. The system and method of the invention further provide the ability to track adverse events in a clinical trial or other setting, thus allowing for these events to perhaps be correlated with other events to aid in determination of the effectiveness and/or potential danger of a particular drug that is the subject of the trial. Furthermore, the clinical trial management application in accordance with this invention is contemplated to be equally applicable to the trial of medical devices or other apparatuses, as well as any method o administration of medication, including ingestion, injection, topical or other appropriate delivery method.

Figure 1:
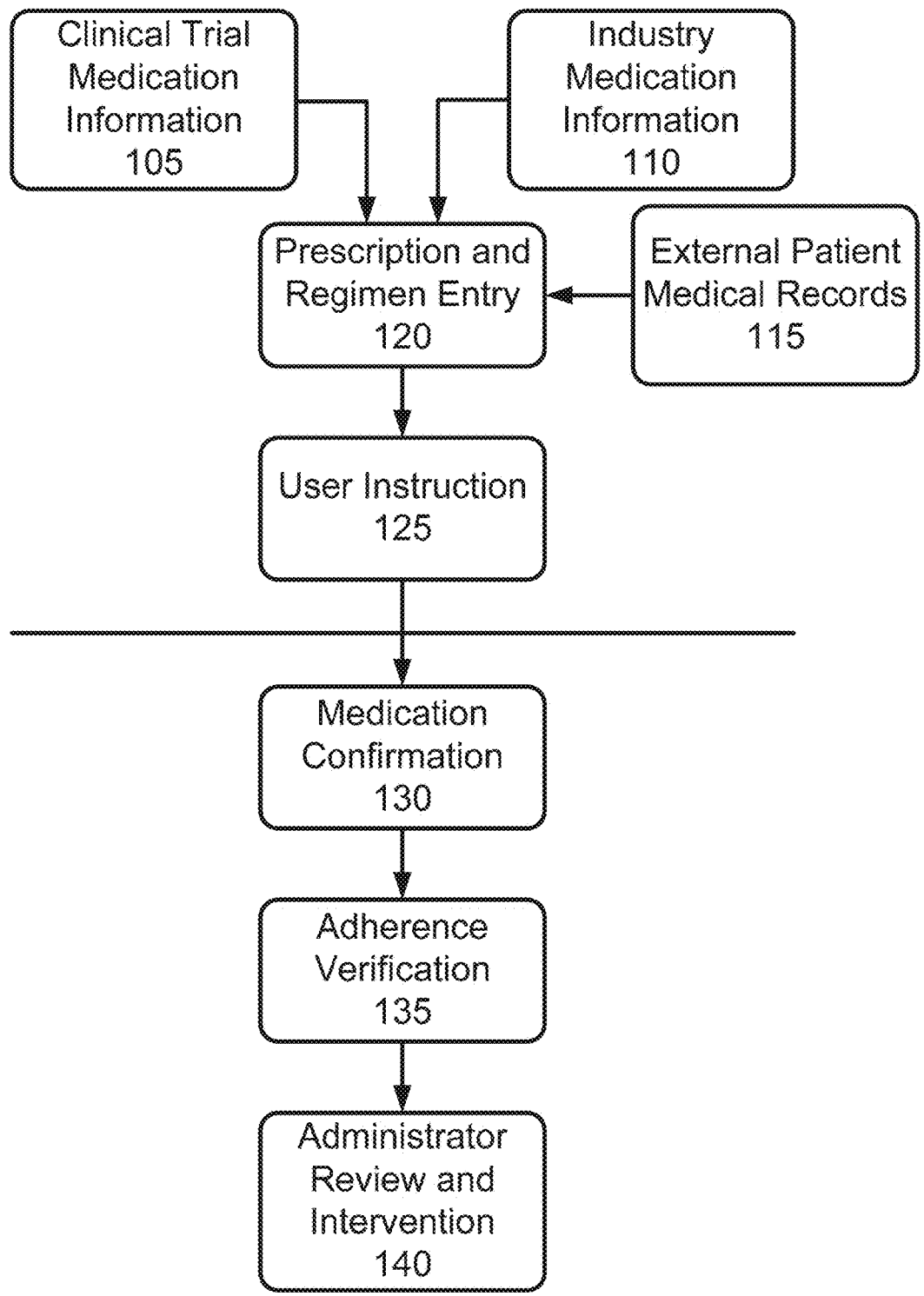
FIG. 1 is a flow chart diagram depicting top level functionality in accordance with an embodiment of the present invention.

Referring first to FIG. 1, a data flow overview is shown. In accordance with the invention, information about a particular drug to be the subject of a clinical trial is provided in a database 105, and existing industry medication information databases 110 are employed to access prescription, interaction, application and other available information about any number of proposed prescription and non-prescription medications and their possible interaction with the clinical trial medication. Further, patient medical records 115 are used, and as will be described below, are used in conjunction with the industry medical information and a medical professional's prescribing expertise to confirm that a patient is a good candidate for such a clinical trial. Once confirmed, a medicine regimen in accordance with the clinical trial requirements is prescribed and entered into the system of the invention at 120. Once entered into the system, a particular prescription regimen causes a set of user instructions 125 to be generated. In accordance with the clinical trial, such instructions may be varied for different users to determine the best set of instructions, or may be varied based upon demographics, experience, or other factors that may require different types of instructions to be provided. It is further contemplated in accordance with the invention that multiple clinical trials may be managed by a manager in accordance with the invention so that the invention contemplates a clinical trial administration system that allows for a single point of management for all clinical trials associated with a particular manager or the like.

Such user instructions may include general instructions about the particular medication subject to the current trial, methods for ingestion, warnings about side effects, concerns about drug interactions with common substances or medications, or other medications prescribed to the patient by the system or by another medical service provider. It is contemplated in accordance with the invention that such set of user instructions may be interactive, allowing a user to view additional information about such instructions or prescriptions as desired. These instructions may comprise written, audio or video instructions. Furthermore, it is contemplated in accordance with the invention that at various points during the instruction set, for example when a patient asks a particular type of question, or asks to receive additional information about a particular aspect of the medication or prescription regimen, that the system may reach out and contact a representative of a medical service provider to provide the patient with additional, personal help as necessary, if it is determined that such intervention by the medical professional would be desirable to the patient. Thus, such a patient may be assisted in properly taking medication so that various errors do not take place. Indeed, in more traditional scenarios, it is only after perhaps finishing a prescription regimen and a return to a doctor in accordance with a predetermined clinical trial schedule that it is discovered that the medication may have been taken incorrectly. In accordance with the present invention, early intervention with such issues can be exercised to deter any possible unfortunate outcomes from improper administration of medication, and to ensure that the particular patient is able to remain in the study and provide accurate data to the study.

It is contemplated in accordance with the invention that a clinical trial manager is provided with a patient dashboard for managing regimes for one or more of the patients taking part in the clinical trial, and as noted above, for managing multiple clinical trials taking place and managed by the particular manager. Such a dashboard allows the clinical trial manager to monitor any number of patients in a manner that will be described below, allow statistical analyses of patient adherence and other patient reactions, provide links to information, including recorded activity sequences for one or more patients, record and be made aware of any adverse events taking place during the trial, and generally allow the medical professional to monitor and administer medication to all of trial participants from a convenient single access point. Such a dashboard also allows for monitoring of any health care providers that may be administering medication to a number of the clinical trial participants, or review of one or more administration sequences or the like.

Additionally, it is contemplated in accordance with the invention that the patient is provided with a user interface dashboard or the like allowing of modification of prescription regimen and instruction information by the patient, limited of course to within guidelines established by the prescribing medical provider. Thus, by way of example, if a user is to take a particular medication before eating in the morning, the user may be able to determine when a reminder for such medication will be given. If the patient is an early riser, the reminder may be provided by cell phone or email at 6:00 AM. Conversely, if the patient sleeps late and normally does not eat an early meal, reminders can be set for later in the morning, thus matching a patient's schedule. Of course, any such patient adjustments must be set within broader prescription regimen as defined by the prescribing medical provider. These requested modifications may give additional information to the trial managers regarding easier protocols for drug administration, or may lead one to investigate a particular individual for non-adherence to the trial protocol.

It is contemplated in accordance with the invention that a touch or other user friendly graphical user interface be provided so that the user can easily manipulate any number of prescription factors, and perhaps enter additional information that may be useful to a prescribing medical provider, such as level of fatigue, level of hunger, jitter inducing medications, etc. All of these data collection points allow for a smoother administration of medication to a patient, and therefore a more likely chance of adherence to a prescribed protocol.

Referring to the lower portion of FIG. 1, the horizontal line indicates a time for patient ingestion or other administration of medication. The patient may display a medication container and/or an actual pill or other medication form to an imaging apparatus, and the apparatus confirming that the medication is correct and is the currently prescribed medication to be taken through the user of text recognition, pill recognition, or other appropriate medication recognition scheme. This sequence of steps therefore acts as an audit trail each time a medication is taken, that can be reviewed later, to ensure that a patient is properly following a regimen.

In accordance with the invention, confirmation of patient adherence to the prescribed administration schedule for the medication as prescribed by the clinical trial regimen is determined. While such confirmation may take a number of forms, in accordance with the invention, a preferred method for such confirmation may include capturing a video sequence of the patient actually administering the medication. In a further preferred method, such a sequence for such confirmation may include employing a facial recognition sequence or other biometric confirmation that a particular patient is in fact receiving treatment, but may also provide for the ability to obscure the face or other identifying feature of a user to allow for the storage and use of such images while protecting the identity of the patient, a technique that may be beneficial when a manager is providing a general report about the clinical trial, and not trying to remedy a situation with a particular patient. Activity recognition, gesture recognition or other feature for determining whether a particular subject movement meets a predefined movement sequence may be employed to be sure that the patient is properly taking prescribed medication.

Furthermore, in accordance with the present invention, a video image of the patient actually administering or ingesting the medication may be taken and stored so that actual confirmation may be achieved, rather than simply relying on the patient to state that a particular medication was administered. Such a video image may be captured or stored in any appropriate format given a selected type of activity or gesture recognition that is employed in accordance with a particular embodiment of the invention. Such may include full video, biometric data points, recording of movement of an article, such as a bracelet or the like, affixed to the patient or administrator, use of mapping to provide a stick figure or other body movement tracking technique, or gesture or activity recognition to determine movement or the like. The user may be encouraged to use a particular sequence of movement to be confirmed that they are properly administering the medication according to the protocol, thus reducing the possibility of the potential appropriate movements considered to be "correct." Indeed, various instructional videos or other appropriate training may be provided to a user to insure they properly administer the medication. Finally, in accordance with the invention, if recording of a video of a patient having the medication administered thereto is not possible, the system of the invention will recognize such an issue and request audio confirmation as a next best option. If the audio confirmation is also not possible, then a less reliable method of confirmation, such as a keyboard confirmation by the patient may be accepted. If higher reliability methods of confirmation are not available for an extended period of time, an alarm is preferably forwarded to a medical professional to inquire as to reasons and to remedy any situation that might be wrong in the administration situation.

These steps of confirming identity, confirming medication and confirming administration are then reviewed to verify adherence to the prescribed protocol at 135. Such review is preferably performed automatically by a computing system that is able to align the actual recorded images with ideal or expected images, or through the user of other activity or gesture recognition as mentioned above. In the case of facial recognition and bottle or pill recognition, such techniques are known in the art. With regard to video confirmation of adherence to prescribed medicine administration procedures, such processing may include various stick figure comparison analyses, activity recognition analysis, or other schemes as noted above able to determine whether appropriate actions have been performed by the patient.

The ability to provide automated determination of adherence to proper administration procedures allows for a large number of such images to be review in a short period of time. Even if actual and complete lack of adherence is not able to be determined 100% in each possible situation, the ability to pre screen the administration video captures to remove from further consideration administration situations that are clearly compliant may reduce a number of compliance situations to be reviewed by a medical professional substantially. Additional human review of indications of failure of adherence may be provided, thus insuring proper review of all potentially dangerous situations while greatly reducing the number of images necessary to be reviewed by a human. Thus, multiple benefits of such an automated system are realized, including reducing time to review such images, reducing costs of such review, and improving patient privacy by limiting the number of humans viewing such data, while improving quality.

In an additional embodiment of the invention the imaged sequences used for activity recognition to determine regimen adherence may be further used to check for adverse or other reactions to taking of the medication. Thus, in addition to simply determining proper adherence to a protocol, such activity or gesture recognition may determine any number of different actions that may have been taken by a patient. Thus, actions taken before medication administration, or actions taken after medication administration may give insight into reasons for particular responses, etc. Thus, before administration, in accordance with the invention, activity recognition may determine a current activity of a user. Any subsequent reminders to take a medication may in part be based upon this determined activity. By way of example, if a user is putting on a coat, or is determined to be leaving a residence or other facility or the like, a reminder to take a medication before leaving may be provided, even if earlier than normal, or if medication is portable, the user may be reminded to take the medication with them, and then subsequently reminded to administer the medication via notification on a mobile device. By way of further example, if the user is cooking, a reminder may be given to take the medication a predetermined time before eating. Other scenarios may be possible, thus allowing greater response from the system to ensure proper medication administration by a patient. Additionally, various patient consent issues may be prompted and recorded in accordance with the invention. Patients may ask further additional questions regarding such consent, thus insuring that patients have all of the information they need to make informed consent decisions, and medication providers have proper evidence of such consent.

Similarly, actions after taking medication may give insight into patient responses. Notice of fainting, falling down, lack of motion, facial gestures, gastrointestinal distress or the like may all be logged as adverse reactions to a particular medication regimen, and may allow for adjustment of dosage or prescription instructions in the future for the patient. If adverse reactions are severe, an immediate medication review and contact from a medical professional may be provided to cure the issue. Additionally, the system in accordance with the present invention may be directly tied and be interoperable with a pharmacy or medical provider's systems as administered by the clinical trial manager, thus allowing such recommendations for dosage changes, regimen changes and the like to be forwarded to these professionals automatically. Through such links, reordering medication, dosage changes, medication changes and the like may be automatically provided. Furthermore, ease of providing additional prescriptions can be enhanced as patient, medication and regimen information will already be available to the pharmacist or medical service provider.

After such automatic, or combination of automatic and manual, adherence verification is performed allowing a health care provider or other medical professional to review and verify results of the automatic comparison or direct review of captured activity sequences, and indication of variation from a desired identity, medication or application procedure may request administrator review of the situation, and intervention as may be determined necessary at 140. Such review may be required immediately as an emergency situation may exist, or the patient may gesture or otherwise indicate that help is necessary, or such review may be less urgent, perhaps requiring an electronic communication with suggestions or the like from such an administrator or the like. Additionally, such adherence review may be stored over time for a particular patient, thus allowing for various medication trends to be determined, such as if a patient misses medication at a same time each week, or an indication that one particular health care worker aiding the patient may occasionally give an incorrect medication dosage amount. Thus, in addition to allowing for immediate notice of problems in medication administration, an audit trail for tracking the actions of various health care providers is generated. Such an audit trail allows clinical trial administrators or other medical professional to determine immediately, or upon review of a complete medication regimen, whether a particular patient or group of patients has followed the protocol to the level that allows their results to be used as part of the study. Additionally, levels of adherence may give insight as to the ease of use of a particular regimen, and whether instructions provided to the patient are sufficient to allow for adherence to the prescribed medication regimen.

Therefore, in accordance with the invention as set forth in FIG. 1, a method and system are provided in which patient adherence to a prescribed medication regimen as set forth in a clinical trial scenario can be reviewed, acutely for a particular instance, or over time to determine any changes in behavior of a patient. Because all aspects of such adherence are monitored preferably visually, and do not rely on patient confirmation of medication administration, desires of the patient are taken out of the equation, and a true review of actually procedures used in the medication administration can be studied. Trial managers are therefore able to keep patients on their prescribed regimens, thus reducing the overall cost associated with the clinical trials, and remove patients from the test population when they cannot maintain adherence to the prescribed regimen, thus increasing the accuracy and repeatability of the results of the trial. Through the management of multiple clinical trials, patient interaction is eased, and any similarities across trials may also be determined, thus improving quality of care generally and allowing for consistency across any number of trials.

Figure 2:
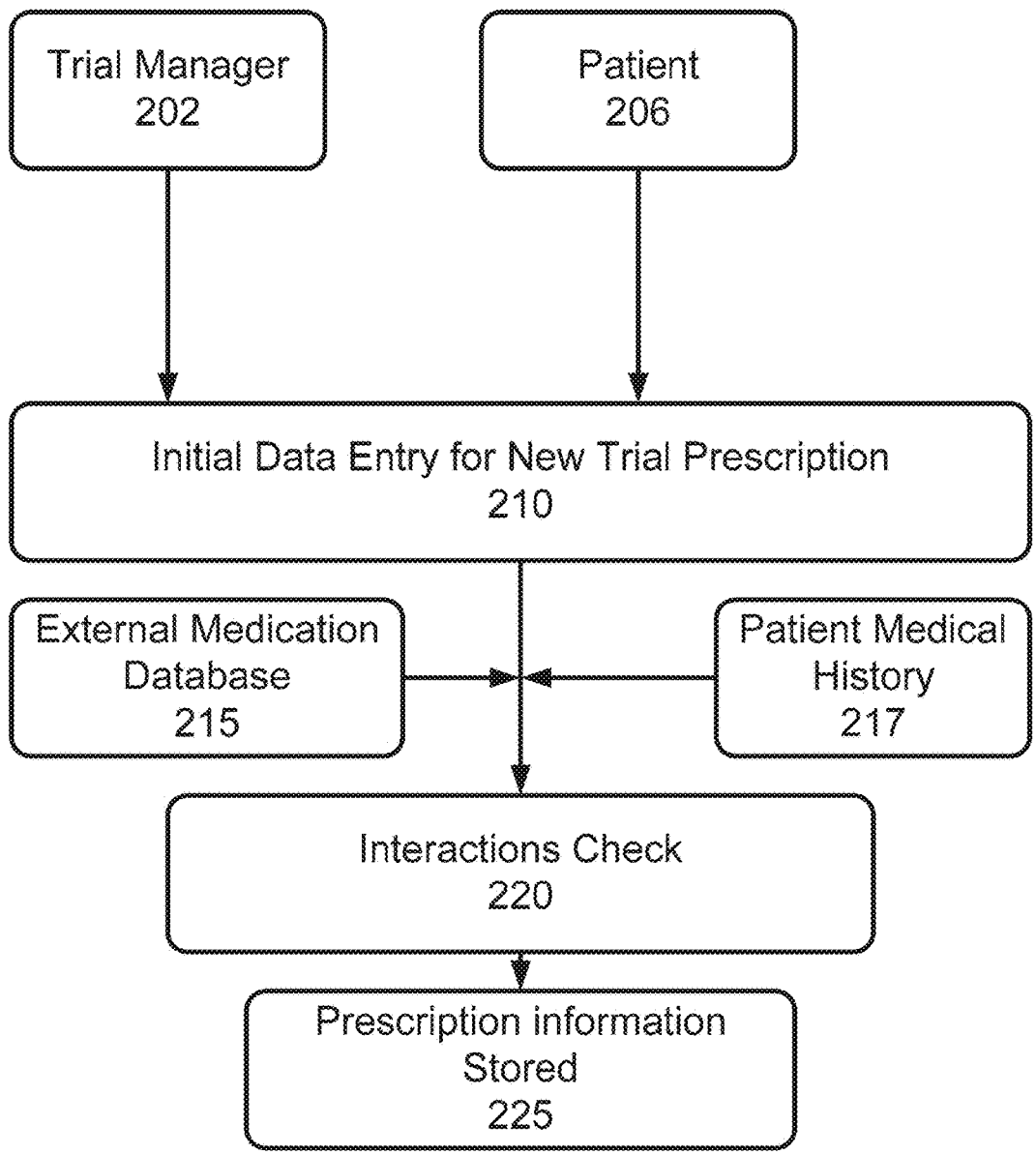
FIG. 2 is a flow chart diagram describing a data entry and prescription assignment process in accordance with an embodiment of the present invention.

Referring next to FIG. 2, a more precise description of the data, medical record and prescription regimen entry will now be described. As is shown in FIG. 2, a clinical trial manager 202 enters information into a system in accordance with the invention, and in particular enters information regarding medication regimen, dosage, instructions sets and the like. A patient 206 may also enter information relevant to the patient. The trial manager 202 may further enter or alter patient information, basic medical statistics, and virtually all other medical information included in a database. The patient 206 may be limited to providing personal information, and perhaps other relevant information, such as non-prescription medication usage, alcohol consumption, recent symptoms, reaction to use of particular prescription medications and the like. Such data entry allows for the tracking of an audit trail at this step of administration as well. Of course, any of this information may be automatically entered into a system from a database having been previously entered or otherwise obtained from an existing data storage area. Also, if particular information is omitted by the patient, or is otherwise unavailable, it might be possible to request provision of this information, or otherwise remove the patient from the clinical trial. Additionally, determination of failure of proper procedure of the information collector may be determined so that additional training or removal of this individual may take place before a large number of patients are entered into a clinical trial with insufficient information collection.

Information from each user of the system is combined, where available, and formed into a clinical trial medication entry 210. In particular, a preferred list of information that may first be provided in accordance with the invention in order to organize the system may comprise a patient name, a user name, if that user is not the patient, and information to be used to provide various alerts, such as a patient email for prescription reminders, contact information for a doctor or caregiver for emergency contact, mailing address for various bulk and non-urgent communications, and cellular telephone or landline telephone information for patient contact, or the like. Further notifications may be provided to the trial manager 202 so that the manager can monitor patient use of the medication and adherence to the proposed and prescribed medication administration. In addition, in accordance with the invention, facial images of the patient and other people interacting with the system are stored, or other biometric identifiers, such as fingerprint identification, retinal identification, voice recognition, various provided RFID tags or the like may be employed along with more traditional passwords and user names or the like. Of course, if the patient is a returning patient, such information may be extracted from an existing database stored with another, previous prescription.

Next, a user such as the doctor 202 or the pharmacist 204 or nurse, may indicate a particular new or recurring prescription medication to be provided to a user in accordance with the clinical trial. An external medication database 215 is accessed and information regarding such medication is provided, including medication name, suggestions for appropriate prescription dosages based upon patient information and the particular version of the medication to be administered, and usage instructions to be provided to the patient, these instructions being modified or supplemented as necessary by the trial manager. These usage instructions preferably include detailed administration instructions, including time of day, patient status (i.e. before or after eating, after waking, before sleeping, etc.), precise method of application, and other useful instructions for a user. These instructions also may include video sequences to describe particular details of the medication or administration procedure thereof and in order to properly indicate gestures to be implemented by the patient. They may also comprise alternative versions of instructions so that if a user is unclear regarding a particular set of instructions, an alternative set of instructions may be provided to the patient to aid in adherence to the prescription regimen.

After selection of such a medication, a patient medical history 217 is preferably accessed to provide additional medication and patient information to the trial manager. Such information may include, other prescriptions to the patient so that adverse drug interaction may be determined (although if such other prescriptions were implemented in accordance with this invention, such prescriptions will already be known to the system), patient indication of use of non-prescription drugs, patient allergies, patient activity level, past diseases and procedures, and any other information that may be relevant to the prescription of medication.

After all of the information has been entered about the user, and information from the medication and patient database has been accumulated, various medication interactions are checked automatically by the system at step 220. Any dangerous interactions are noted to the trial manager, and may preclude entry of the prescription into the system and therefore preclude the particular patient from participating in the clinical trial. Other interactions may be noted to the trial manager so that the individual may make the patient aware of such situations. These may include, for example a notification that the taking of two medications together may result in stomach pains, so that the patient should take one in the morning and one in the afternoon. Such interactions check will then result in a set of instructions that will be provided to the user, in addition to the more generic medication instructions. Finally, the trial manager may review such instructions and supplement them as desired. It should be noted that in accordance with the invention it is contemplated that various instructions provided to a user may comprise hot links to additional audio and visual information that may be provided to a patient to further assist in their adherence to any particular prescribed protocol, or may provide various information regarding the particular medication being taken as will be further described below. Such instructions may indicate methods by which a user is to administer one or more medications, and thus requests use of a particular gesture or the like during administration.

Finally, after all interactions and instructions have been reviewed and approved, the prescription information is stored at step 225. The storing of such a prescription makes the prescription, alerts, help information and the like accessible to a patient and other system users. Furthermore, such completion may also transmit the prescription to a pharmacy or other medication provision facility so that the user is able to simply swing by to pick up the medication or to have the medication delivered to the patient.

Figure 3:
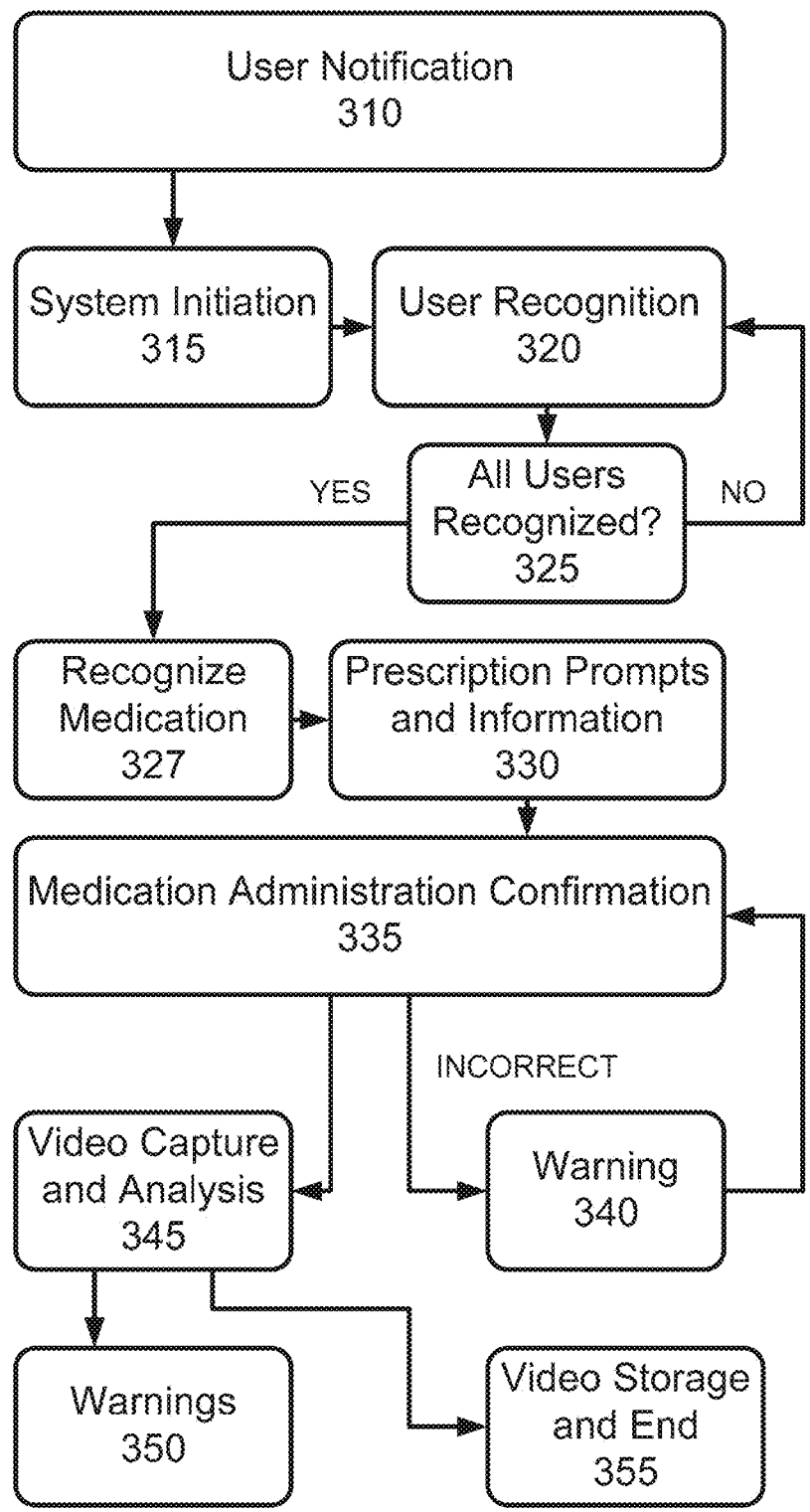
FIG. 3 is a flow chart diagram describing a medical compliance regimen from in accordance with an embodiment of the invention.

Referring next to FIG. 3, a user implementation of the method in accordance with the invention will be described. When a time for receiving or administering a medication in accordance with a clinical trial regimen is reached, a patient, and any other necessary user may be provided a notification 310 in accordance with notification addresses entered in the system as noted above. Thus, in a home situation, only the patient may receive notification. If there is a home health care provider, such provider may also receive separate independent verification. In the case of hospital or other in-patient care facility, various medical service providers may similarly receive such notification. After notification, or in the absence of such notification, system initiation takes place at 315. In accordance with such system initiation, one or more users are preferably recognized by the system. Therefore, at step 320, a user recognition sequence takes place. In a preferred embodiment, such a user has a still or video image captured of their face, and facial recognition techniques are employed to confirm the identity of the user. Such capture may be performed by fixed camera, mobile camera, mobile communication device such as a cellular phone, or any other appropriate video or image capture device. Alternative recognition techniques, such as retinal, fingerprint, voice or other biometric measurements may be employed, in addition to a more common password query. Any other appropriate identification technique may be employed, and any unique individual identifiers may be obscured, as noted above, when the images are to be used as a more general report regarding adherence, rather than an individual patient response.

At step 325 it is determined whether all necessary users have been recognized and authenticated. In a situation where a nurse, doctor or other caregiver is to administer medication, it may be preferable to have the patient and caregiver to be recognized by the system to further confirm that the appropriate procedure is followed, and to allow the system to keep track of people using the medication so it can track if any one person, for example, is improperly using the medication, as will be evident from the generated audit trail. After step 325, if all users are not recognized, control passes back to step 320 and any additional users are recognized by the system.

Once all users are recognized, control passes to step 327 where the medication to be administered in accordance with the prescribed prescription regimen of the clinical trial is confirmed. Thus, a user is prompted to allow a still or video image, text recognition image, or other method of identifying a medication to be captured of the medication bottle or other container, a pill of the medication, or other form of medication, and is also able to determine appropriate quantities, dosage, and any potentially required or dangerous medication combinations. As noted above, if video confirmation is for some reason not available, the user may be prompted by the system to provide audio or other indication of medication and other desired information. This image, video sequence or other received confirmation information is then compared to an image associated with the prescription as noted above in FIG. 2. If the medication is determined to be incorrect, a warning may be provided to the user that the medication is incorrect. The user may then be prompted to choose another medication for imaging.

Alternatively, the invention contemplates a user displaying a number of medications to the image capture apparatus and allowing the apparatus to suggest which medication is correct. Thus, the user may be able to scan a medicine cabinet with such a video imaging apparatus and have the system indicate which is the correct medication. This may prove valuable when sequence of ingesting medication is important, or when two people have similar medications and may have difficulty in distinguishing between medications for each. Once a correct medication has been identified, control passes to step 330.

In step 330 user prompts and other instructions are provided to the patient, and present caregivers, as to how to administer the medication according to the prescription guidelines outlined above as determined in accordance with the particular clinical trial under consideration. These instructions allow for a user to receive further information or instructions as necessary through asking the system for additional help. Especially in situations where an elaborate scheme may be required, it is contemplated that video samples and instructions may be provided to the user. Further, in accordance with the invention, for complicated administration procedures, it may be possible to set up a two way video conference employing traditional video conferencing, VOIP conferencing, traditional telephone conferencing, or any other appropriate communication system with an expert in such administration so that a caregiver or patient may receive live coaching regarding such administration. Such instructions and prompts may be determined by the clinical trial manager to determine the success or failure of particular sets of instructions. Thus, not only are medications tested in such a clinical trial, but also sets of instructions are tested to determine which are best for all, or for giver demographic groups or the like for eventual user when the medication is released to the public, thereby allowing for a better adherence rate by the public. As the number of clinical trials grows, and the locations of such trials becomes more international, such administration through a system such as that set forth in accordance with the invention may become far more important to various clinical trial managers.

When following such instruction prompts, the actual act of administration is preferably captured as a video sequence at step 335. Thus administration preferably includes one or more identifiable gestures as suggested in accordance with the instructions above. Thus, a patient or administrator may be provided with one or more images or sequences for method of application or administration, and thus the following of these sequences is used to determine compliance with a particular prescribed regimen. Further, long gaps or pauses may be determined to give further insight into areas of administration that may be giving problems to administrators of trial participants. This captured video sequence may be utilized in accordance with the invention in a number of ways. First, the actions of administration of the medication is reviewed in real time and compared to an ideal or desired video sequence. If a determination is made that the medication is being administered in an incorrect manner, and in a way that may be detrimental to the patient, immediate warnings may be provided at step 340 advising the caregiver or patient to stop administration at once. Furthermore, in extreme cases, a doctor or other caregiver may be notified, or in the most dangerous cases, an ambulance or other emergency personnel may be dispatched to provide immediate care. Notification may also be provided to the clinical trial manager so that this person is warned that one or more patients are having problems with adherence with the protocol. If such problems turn out to be isolated, alternative instructions, or personal help may remedy the situation, thus allowing the person to provide meaningful data to the trial. If such lack of adherence is far more widespread, the clinical trial manager may change instructions for all participants, or may even ask all participants to come back in for further live instructions. In either situation, the cost of the clinical trial is greatly reduced as participants are able to remain in the study, and major failures of studies for lack of protocol adherence may be avoided. Reports based upon such widespread lack of adherence may provide a manager with a report, using images or the like with identifying features removed so that the report may show precisely how a medication is being administered while maintaining patient privacy and confidentiality. If video recording is not available, other confirmation methods as noted above may be employed and be subject to automatic confirmation as with the video recorded sequences.

If such immediate care or warning is not required, control then passes to step 345 where the video images are more formally captured and analyzed for various other non-critical issues. The images may be captured and stored locally, being provided to a central server in a batch processing, or images may be captured and sent to the remote server for immediate analysis and storage. Such transmission may take place over a well known Internet connection, wireless connection, or other proprietary communication system. Such analysis may consider suggestions to a caregiver to improve dosage accuracy, reduce pain in administration, or the like. These suggestions may be implemented as tweaks to various instruction or training sequences before the medication is released to the general public. Furthermore, as such video sequences may be available from multiple patients and/or caregivers taking part in the current or multiple clinical trials, the effectiveness of various sets of instructions and the like can be tested and reviewed, and changes thereto made if consistent problems are encountered. This type of study is nearly impossible without the present invention, because in any type of clinical setting, individuals are far more likely to be careful in administration of medication, and therefore not cause errors. When they return home or back to their regular lives, this is when adherence and administration issues arise. In accordance with the invention, responses to instructions can be analyzed, and lack of adherence based upon confusing or difficult to follow instructions can be remedied, providing better or more usable instructions, and therefore improving regimen adherence. Without the present invention, such a clinical trial manager may be unaware of such issues. With the invention, these issues can be addressed as they arise, thus ensuring the integrity of the clinical trial.

In any event, after such analysis, any warnings or suggestions for instruction issues may generate a warning at step 350, suggesting areas of instruction that may be problematic. These video sequences are also stored for longer term analysis if desired at step 355, and processing ends. Furthermore, in order to encourage patients in the clinical trial, notices of lack of adherence may be used to change remuneration received by a patient in the clinical trial. Thus, adherence to the protocol results in higher payments to the patient, a great incentive for the patient to adhere to the protocol.

Trends of a patient taking part in the clinical trial can be monitored, such as blood pressure or other measurable quantities of the patient, and correlation between such measured quantities and medication administration may be observed, potentially allowing for a more customized solution of medication to be applied to the patient, possible modifying dosage or frequency of administration based upon individual reactions to a particular prescription regimen. Additionally, features of the invention noted above allowing for user interaction and recordation of activities of a user, adverse effects and the like may be incorporated into the system to provide further information for determining alternative instruction sets, modification of medications and the like.

Figure 4:
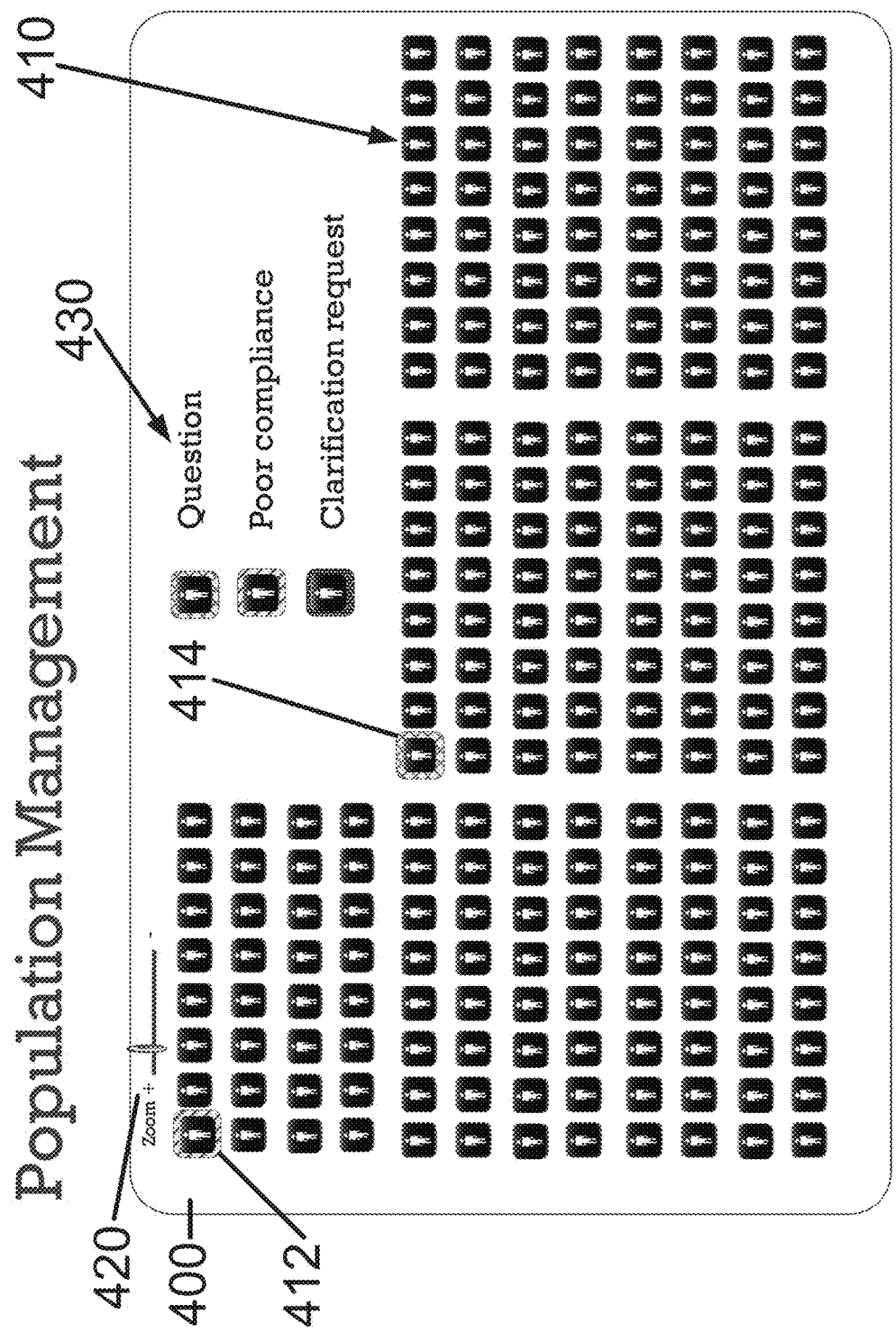
FIG. 4 is a representation of a summary page of a dashboard in accordance with a preferred embodiment of the invention.
Figure 5:
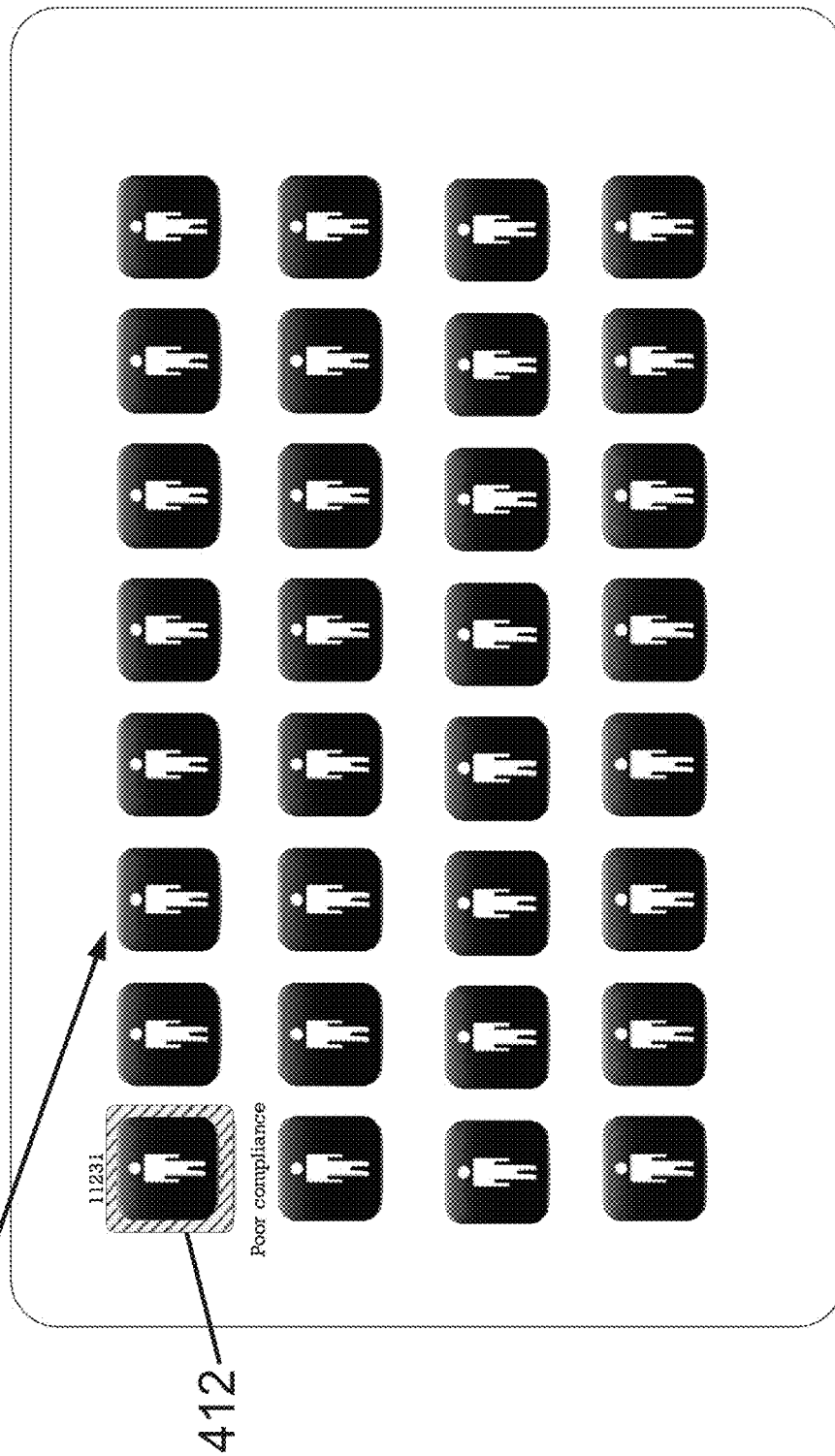
FIG. 5 is a representation of a zoomed in view of the summary page of FIG. 4.

It is further contemplated that the clinical trial manager be provided with a manager dashboard allowing for summary review of all patients taking part in one or more clinical trials. Details of an exemplary embodiment of such a dashboard will now be described making reference to FIGS. 4-6. As is shown in FIG. 4, a summary page dashboard is shown at 400. Each different clinical trial is contemplated to have one or more summary pages (as more than one page may be necessary for a particular clinical trial given the number of participants). Each summary page includes indicators 410 for each participant taking place in a particular clinical trial. In FIG. 4 such indicators are shown as icons representing each person. Such icons may be replaced with summary identification information or the like, or any other desired indicator, such a demographic indicators (i.e. age group, sex, medical condition, individual characteristics, etc.) Also included in dashboard 400 is an indicator legend including information that may be applied to any one or more of the indicators 410. In this particular preferred embodiment of the invention, the indicator legend includes indicator modifiers representing that a particular trial participant asked a question, has a report of poor compliance, or requested clarification of some instruction or other facet of the clinical trial. As is shown, each indicator modifier may be applied to a particular indicator 410 to which the modifier applies. Thus, as is shown in FIG. 4, indicator 412 has been flagged for poor compliance, while indication 414 has been flagged as asking a question. Thus, in this manner, a clinical trial manager is provided with an overview of the status of the patients in a clinical trial. Major compliance problems would be easily determined by the clinical trial manager viewing a dashboard with many of the indicators 410 being modified by the indicator modifier related to poor compliance. Similarly, problems with instructions might be apparent if the summary display indicates a large number of questions or clarification requests. Of course indicator modifiers for any number of other situations may be provided. Statistical analysis of the population of the clinical trial may also be provided, thus allowing for the clinical trial manager to determine adherence rates and other metrics of the entire or subsection of the clinical trial population. Such modifiers are preferably color indicators, but may comprise any other appropriate indication that allows the clinical trial manager to determine status.

Dashboard 400 further preferably includes a zoom indicator that allows the clinical trial manager down to each patient or a smaller number of patients to view their overall compliance statistics, or to view individual recorded video sequences, requests for additional information, or any other information stored as the audit trail for patients in accordance with the invention. Thus, if the zoom indicator is zoomed all of the way out, the clinical trial manager is presented with the largest number of indicators 410 on the dashboard. A medium zoom preferably provides the clinical trial manager with a view such as that shown in FIG. 5. As is shown, indicator 412 includes additional information adjacent the indicator. In the displayed situation, the name for the indicator modifier is shown. This may be beneficial when a large number of indicator modifiers may be provided. Alternatively, this text might include a most critical piece of information, or a user selected piece of information. The zoom feature may also allow the clinical trial manager to zoom down by demographic information of the like, thus viewing indicators 410 representing clinical trial participants having similar characteristics in one form or another.

In addition, it is contemplated that the clinical trial manager may use the summary dashboard, at any desired level of zoom, to select and move, modify, or otherwise act upon a subset of indicators included in a clinical trial. Thus, one or more participants may be assigned to different populations, grouped as desired to receive different instructions, dosages, or have any other modification of medication administration applied to the selected group of participants. Participants may also be grouped based upon prescribing medical provider, clinic, medical group, insurance company, or in any other manner that might be considered useful to the clinical trial manager. By grouping by these groups, it may be possible to determine if any particular clinic, doctor or the like results in poor compliance for that group. Thus, poor compliance linked to a particular such group can also be addressed through, perhaps, additional training for the clinic or doctor. Participants may also be added to, or deleted from a particular trial or other epidemiological study or the like, if desired, or otherwise manipulated. Groupings may also be automated, such as grouping all patients by age, gender, or other demographic characteristic, thus providing a quick useful view to the clinical trial manager.

Figure 6:
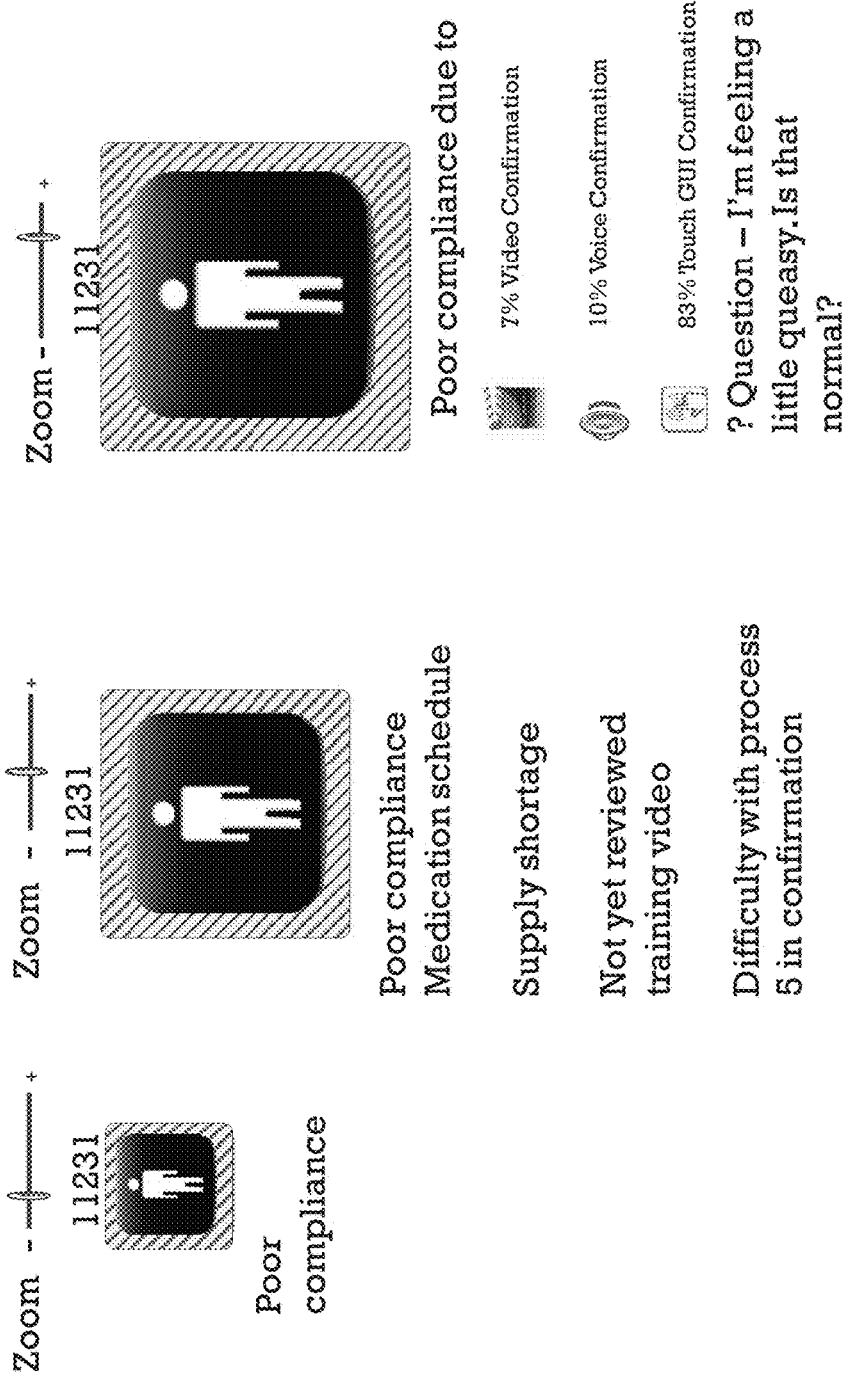
FIG. 6 is a representation of information provided in accordance with an individual clinical trial participant indicator in accordance with a preferred embodiment of the invention.

Further zooming in allows the clinical trial manager to view a smaller number of indicators, down to a single indicator. As the number of indicators decreases, the amount of information available to the clinical trial manager for each indicator increases. Thus, the clinical trial manager may zoom down to one of the possible levels as shown in FIG. 6. As is shown in FIG. 6, the first zoom level shows the level of information of FIG. 5, while a great number of indicators 410 are still visible. A more detailed zoom level preferably displays The same poor compliance indicator, but further shows that this poor compliance is related to the medication schedule, and in particular a supply shortage of the medication, thus providing a more complete compliance check of the clinical trial participant. The information further provides poor compliance information in that the participant represented by the indicator has not yet reviewed a required (or suggested) training video, and is also having difficulty with a fifth process in the defined confirmation scheme. Finally, a further zoom level, after indication a desire to have more information regarding the poor compliance indicates that the participant has only had 7% of their actions confirmed by video, 10% confirmed by voice, and the remaining 83% confirmed by GUI interface (which is patient dependent and therefore is not determined to be as reliable as the other two methods). Furthermore, the participant has asked a particular question. From this particular zoom level, it is contemplated that the clinical trial manager may directly link to the stored video, audio or GUI provided information. Preferably, a timeline or the like is provided to the clinical trial manager indicating when the various, video, audio and/or GUI entries have been stored. The clinical trial manager is able to view an even more useful picture of the sequence of compliance, and is then able to select any of the stored sequences for review. The manager may also answer the question, or forward the question to a physician or the like who is appropriate to answer the question. The clinical trial manager may also opt to change instructions provided to one or more patients in accordance with their record of adherence when being exposed to a first set of instructions. This level of zoom may also provide links for allowing communication with a particular participant, and method for suggesting additional training, instructions or help, and a process for ordering or providing additional medication to a participant. Specific instructions to a patient, preferences, or comments or the like provided by a patient may also be reviewed. Finally, the clinical trial manager may view upcoming prescription information, including times for taking a prescription or other medication administration applicable to one or more patients.

It is therefore through such a dashboard that the clinical trial manager receives notice of any problematic failures on the part of patients warranting intervention, either by direct contact, changes in regimen or instruction, or recall of the patient for retraining. As noted above, rather than waiting for the patient to come back in and report poor adherence, or worse yet, allowing the patient data to become part of the clinical resultant data even with poor adherence, the clinical trial manager may use the dashboard of the invention to ensure that poor compliance is recognized early and dealt with. Furthermore, emergency situations may be indicated to the clinical trial manager in an immediate manner.

Such a dashboard is preferably provided with patient management features in addition to the notification features noted above. Thus, the clinical trial manager is able to manage individual participants, subsets of the population, or the entire population through drop and/or drag functionality, and is able to broadcast information to these groups as necessary, including the broadcast of video, text, or voice instructions. The clinical trial manager may also preferably remind participants of upcoming doctor appointments, meetings regarding the clinical trial, and also provide such notices to the patient's prescribing physician. Additional medication or supplies may be provided to a participant upon notice that they have run out, or merely tracking of medication actually taken by the participant. Thus, there is no guesswork. The manager may further review patient medical records, as necessary, to further aid in trial procedure compliance.

The dashboard also preferably provides access to medical professionals associated with one or more of the clinical trial participants. In a situation where the trial provides all of the prescribing doctors or other medication administrators, for those patients that may need assistance, this feature may be trivial, but when multiple prescribing doctors are involved in a trial, being able to forward information and interact with these doctors may prove very valuable. Such contact may be made through a link or connection provided associated with each patient identifier icon on the dashboard. Thus, the clinical trial manager may be able to review videos or other compliance indicia with such a prescribing physician, perform remote triage regarding any complications that might arise with a patient during the course of the trial, or request prescription changes, etc. Furthermore, the clinical trial manager may be able to audit these very medical professionals looking after, and administering medication in accordance with the prescribed clinical trial procedure. Through such an audit, the manager may be able to determine issues related to actions of a particular administrator.

A user dashboard may also be provided to allow a participant to enter information, such as GUI entered compliance information as noted above, but also to ask questions, view additional instructions, order supplies, or the like. The user may view more specific prescription regimen information, such as when a next medication is scheduled to be taken, or be provided with a calendar for a predetermined future time period to allow for future planning. Through such a user dashboard, the user may view particular information relevant to their treatment, but preferably not enough information to influence their participation in the trial. If in use, a participant may also view whether they have achieved various adherence levels resulting in payments to be made to them in accordance with the invention. Furthermore, the user may be provided with a method for determining a level of data transmission, including identity information that may be provided to various level of administrator. Thus, while all information may be provided to a clinical trial manager, perhaps more limited identifying information may be made available to other researchers or the like. The participant may be notified as to potential uses, and an opt in or opt out set of choices for such different levels of disclosure. The user may be provided with a privacy setting indicator to indicate a level of availability of recorded information and attachment of identifying information thereto.

Thus, provision of such a dashboard in conjunction with the operative clinical trial verification process and system described above eases use, increases effectiveness and allows for better control over such a clinical trial. Difficulties in following protocols may be determined in near real time. Changes in a trial may be easily implemented and conveyed to trial participants and their prescribing doctors. New training modules, including video, written, or other instructions may be provided during a trial in order to improve adherence. Inventory management is eased and all trial participants are sure to have the appropriate amounts of medication and other supplies. Further, a full audit trail of who has accessed information for any particular patient, groups of patients, or one or more clinical trials is maintained. This dashboard, however, is not limited to use only in a clinical trial. Rather, the system can be used by a single medical provider, doctor group or network, insurance company, governmental agency, nursing home, hospice, home care provider or the like, or other group in order to track any number of patients and associated home care workers, doctors, or other medication administrators. In such scenarios, the ability to view, group, and retrieve significant information about particular patients allows for greater control over these patients, resulting in reduced likelihood of a patient continuing to take improper medication, or to improperly administer such medication, and therefore in turn reducing the possibility of an adverse reaction or death from a particular medication.

A system provided in accordance with the invention includes imaging technology and hardware, communication hardware, computer systems including storage memory and remote communication via the Internet or other communication network for remote storage and analysis, databases of patient information and medication information sufficient to implement the method as described above. All communications are encrypted or otherwise protected during transmission and storage at both local and remote mass storage location to meet any security issues and any regulations required for the storage and maintenance of medical and patient health care information.

Therefore, in accordance with the invention, a method and system are provided that allow for the automated confirmation of adherence to administration protocol for medication in a clinical trial environment, and provide for a most sophisticated method for confirming and studying methods of administration of such prescription medication.

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that this description is intended to cover all of the generic and specific features of the invention herein described and all statements of the scope of the invention which, as a matter of language, might be said to fall there between.

What is claimed:

1. A method of confirming administration of medication, comprising:
    identifying a particular medication prescription regimen;
    predefining one or more identifiable gestures indicative of proper administration of the medication in accordance with the medication prescription regimen;
    providing, on a display of a local device, one or more instruction prompts directing performance of the one or more predefined identifiable gestures indicative of proper administration of the medication;
    capturing video activity sequences, by a video capture device of the local device, of a user following the one or more instruction prompts to administer the medication during a current medication administration session;
    storing the captured video activity sequences to a non-transitory computer readable storage medium;
    comparing, by a computer processor, the stored video activity sequences to the predefined one or more identifiable gestures indicative of proper medication administration;
    determining, from the comparison, differences between the stored video activity sequences and the predefined one or more identifiable gestures, wherein the differences indicate that the medication has not been properly administered;
    responsive to determining the differences, providing, on the display of the local device, one or more further instruction prompts that further direct current performance of the one or more predefined identifiable gestures indicative of proper medication administration;
    capturing, by the video capture device, second video activity sequences of the user following the one or more further instruction prompts to administer the medication during the current medication administration;
    storing the captured second video activity sequences to the non-transitory computer readable storage medium;
    comparing, by the computer processor, the stored second video activity sequences to the predefined one or more identifiable gestures indicative of proper medication administration; and
    determining, by the computer processor, that the stored second video activity sequences are sufficiently similar to the predefined one or more identifiable gestures, thus confirming proper administration of the medication.

2. The method of claim 1, wherein the prescription regimen is provided by a healthcare provider.

3. The method of claim 1, further comprising retrieving the prescription regimen and the predefined one or more identifiable gestures indicative of proper medication administration from a medical database.

4. The method of claim 1, further comprising performing a statistical analysis of the differences between the stored video activity sequences and the predefined one or more identifiable gestures.

5. The method of claim 1, further comprising:
    retrieving medical history information of the user to receive the medication to be administered; and confirming, from the retrieved medical history information, that the medication to be administered is safe for the patient.

6. The method of claim 1, further comprising:
before capturing the video activity sequences, determining the identity of a particular medication to be used in the administration of the medication;
determining, by the computer processor, that the identity of the particular medication is not the same medication associated with the prescription regimen; and
issuing a warning responsive to determining that the identity of the particular medication is not the same medication associated with the prescription regimen.

7. The method of claim 1, comprising:
capturing, by the video capture device, a plurality of video activity sequences of the user following the one or more instruction prompts during a plurality of different medication administration sessions;
transmitting the captured video activity sequences from the plurality of different medication administration sessions to a remote server location;
further analyzing, by a computer processor of the remove server location, the plurality of captured video activity sequences by comparing each captured video activity sequence, of the plurality of captured video activity sequences, to the predefined one or more identifiable gestures to determine differences therebetween, thereby automatically determining that one or more of the predefined one or more identifiable gestures have been improperly performed by the user across one or more of the multiple medication administration sessions; and
providing an analysis of adherence to the particular prescription regimen based on the comparison of each captured video activity sequence, of the plurality of captured video activity sequences, to the predefined one or more identifiable gestures.

8. The method of claim 7, further comprising providing modified instructions directing performance of the one or more predefined identifiable gestures indicative of proper medication administration to a medication administrator in accordance with the provided analysis.

9. The method of claim 1, wherein the computer processor for performing the steps of comparing is located remote to the local device.

10. The method of claim 1, wherein the notice comprises additional instructions via the display of the local device to a patient receiving the medication according to the medication administration procedure.

11. A system for confirming administration of a medication, comprising:
an authentication apparatus operable to authenticate a healthcare provider;
an input device operable to receive information identifying a particular medication prescription regimen from the authenticated healthcare provider;
a storage device operable to store prescription administration information associated with the identified medication prescription regimen, a predefined set of one or more identifiable gestures indicative of proper administration of the medication in accordance with which the prescription regimen is to be administered, and one or more instruction prompts directing performance of the one or more predefined identifiable gestures indicative of proper medication administration;
a video capture device;
an audio and/or video output device operable to output the one or more instruction prompts directing performance of the one or more predefined identifiable gestures indicative of proper medication administration; and
a processor operable to perform operations comprising:
capturing, from the video capture device, video activity sequences of a user administering the medication by following the one or more instruction prompts directing performance of the one or more predefined identifiable gestures indicative of proper medication administration;
storing the captured video activity sequences to the storage device;
comparing the captured video activity sequences to the one or more predefined identifiable gestures indicative of proper medication administration;
determining that the stored captured video activity sequences are different from the one or more predefined identifiable gestures indicative of proper medication administration, indicating that administration of the medication has not been properly performed;
responsive to determining that the stored captured video activity sequences are different from the one or more predefined identifiable gestures, causing the audio and/or video output device to output one or more further instruction prompts for further directing performance of the one or more predefined identifiable gestures indicative of proper medication administration during a current medication administration session;
capturing, from the video capture device, second video activity sequences of the user administering the medication by following the one or more further instruction prompts;
storing the second captured video sequences to the storage device;
comparing the stored second video activity sequences to the one or more predefined identifiable gestures indicative of proper medication administration; and
determining that stored second captured video sequences are sufficiently similar to the one or more predefined identifiable gestures, indicating that proper medication administration was successful.

12. The system of claim 11, wherein the processor is located remote from the video capture device.

13. The system of claim 11, wherein the video capture device is further operable to capture images of a particular medication to allow identification thereof.

14. A method of confirming proper administration of medication, comprising:
authenticating a prescribing health care provider;
receiving information identifying a particular medication prescription regimen from the authenticated health care provider;
modifying the particular medication administration regimen by the authenticated health care provider;
providing, on a display of a local device, one or more instruction prompts directing performance of one or more predefined identifiable gestures, the one or more instruction prompts comprising visual indicia indicative of proper ingestion of the medication;
capturing, by the local device, visual indicia of a user following the one or more instruction prompts to administer the particular prescription regimen during a current medication administration session;
storing the captured visual indicia to a non-transitory computer readable storage medium;

comparing, by a computer processor, the captured visual indicia to the one or more predefined identifiable gestures to determine one or more differences; and providing, in response to determining the one or more differences, a notice, on the display of the local device, one or more further instruction prompts for further directing a performance of the one or more predefined identifiable gestures during the current medication administration session.

15. The method of claim 14, wherein the visual indicia comprises one or more video activity sequences.

16. The method of claim 14, further comprising:
capturing, by the video capture device, additional visual indicia of activity of the user before the user administers the medication; and
providing a reminder to the user at least in part in accordance with the captured additional visual indicia before the user administers the medication.

17. The method of claim 14, further comprising capturing, by the video capture device, additional visual indicia of activity of the user by before the user administers medication, wherein the captured additional visual indicia comprises evidence of patient consent.

18. The method of claim 14, further comprising:
capturing, by the video capture device, additional visual indicia of activity of the user after the user administers the medication;
providing notification to a medical service provider of the activity of the user after the user administers the medication; and
modifying at least one aspect of the particular medication prescription regimen in accordance with the captured additional visual indicia.

19. The method of claim 14, wherein the computer processor is located remote from the local device.

* * * * *